(12) United States Patent
Krivonos et al.

(10) Patent No.: US 8,344,165 B2
(45) Date of Patent: Jan. 1, 2013

(54) CRYSTALLINE ROTIGOTINE BASE AND PREPARATION PROCESS THEREFOR

(75) Inventors: Sonia Krivonos, Beer Sheva (IL); Alex Weisman, Kiriat Ekron (IL)

(73) Assignee: CHEMAGIS Ltd., Bnei Brak (IL)

( * ) Notice: Subject to any disclaimer, the term of this patent is extended or adjusted under 35 U.S.C. 154(b) by 296 days.

(21) Appl. No.: 12/601,749

(22) PCT Filed: May 28, 2008

(86) PCT No.: PCT/IL2008/000721
§ 371 (c)(1),
(2), (4) Date: May 17, 2010

(87) PCT Pub. No.: WO2008/146284
PCT Pub. Date: Dec. 4, 2008

(65) Prior Publication Data
US 2010/0222602 A1    Sep. 2, 2010

Related U.S. Application Data

(60) Provisional application No. 60/940,910, filed on May 30, 2007.

(51) Int. Cl.
*C07D 333/12* (2006.01)

(52) U.S. Cl. .......................................................... 549/75
(58) Field of Classification Search ...................... 549/75
See application file for complete search history.

(56) References Cited

U.S. PATENT DOCUMENTS

| 6,372,920 | B1 | 4/2002 | Minaskanian et al. |
| 2004/0048779 | A1 | 3/2004 | Schollmayer |
| 2005/0175678 | A1 | 8/2005 | Breitenbach |

FOREIGN PATENT DOCUMENTS

| EP | 1 325 742 A1 | 7/2003 |
| WO | WO 2004/058247 A1 | 7/2004 |

OTHER PUBLICATIONS

International Search Report dated Dec. 22, 2008 for PCT/IL2008/000721.

*Primary Examiner* — Taofiq A Solola
(74) *Attorney, Agent, or Firm* — Leydig, Voit & Mayer, Ltd.

(57) ABSTRACT

An isolated and pure crystalline rotigotine base of polymorph Form I, and processes for producing the crystalline rotigotine base are disclosed. Also disclosed is a transdermal patch for the delivery of rotigotine base using the disclosed isolated and pure form of rotigotine base, which can be used in treatment of Parkinson's Disease and other disorders ameliorated or treated by rotigotine, including restless leg syndrome.

11 Claims, 4 Drawing Sheets

CRYSTALLINE ROTIGOTINE BASE AND PREPARATION PROCESS THEREFOR

CROSS-REFERENCE TO RELATED APPLICATIONS

This patent application claims the benefit of U.S. Provisional Patent Application No. 60/940,910, filed May 30, 2007, which is incorporated herein by reference.

TECHNICAL FIELD

The present invention relates to organic chemistry and more particularly to crystalline rotigotine base and processes for preparation and purification therefor.

BACKGROUND OF THE INVENTION

Rotigotine ((S)-(−)-5-hydroxy-2-(N-n-propyl-N-2-thienylethyl)-aminotetralin) is represented by the following structural formula:

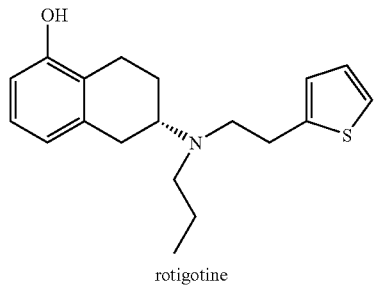 [SMILES: CCCN(CCc1cccs1)[C@H]1CCc2c(O)cccc2C1]

rotigotine

Rotigotine is a non-ergolinic dopamine-receptor agonist, which is used for the treatment of the signs and symptoms of early-stage idiopathic Parkinson's disease. The drug is administered via a silicon-based transdermal delivery patch.

Rotigotine is sold in Europe by Schwarz Pharma as NEUPRO® and was recently approved by the FDA for use in the U.S. NEUPRO® is formulated as 10 $cm^2$, 20 $cm^2$, 30 $cm^2$, and 40 $cm^2$ transdermal patches containing 4.5 mg, 9.0 mg, 13.5 mg and 18.0 mg rotigotine per base, respectively, designed to release 2 mg, 4 mg, 6 mg and 8 mg, respectively, of rotigotine per 24 hours.

The preparation of racemic rotigotine hydrochloride is disclosed in U.S. Pat. No. 4,564,628. The process, which is depicted in Scheme 1, comprises reacting 5-methoxy-2-tetralone (Compound I) with β-(2-thienyl)ethylamine in presence of p-toluenesulfonic acid and sodium cyanoborohydride to obtain 1,2,3,4-tetrahydro-5-methoxy-N-[2-(thienyl)-ethyl]-2-naphthaleneamine (Compound II), which is reacted with propionyl chloride in presence of triethylamine to obtain N-(1,2,3,4-tetrahydro-5-methoxy-2-naphthenyl)-N-[2-(2-thienyl)ethyl)]propaneamide (Compound III). This propanamide is reduced with lithium aluminum hydride to obtain 1,2,3,4-tetrahydro-5-methoxy-N-propyl-N-[2-(2-thienyl)ethyl]-2-naphthaleneamine (Compound IV), which is subsequently reacted with boron tribromide, then hydrochloric acid (HCl) to form the racemic rotigotine hydrochloride (Compound V).

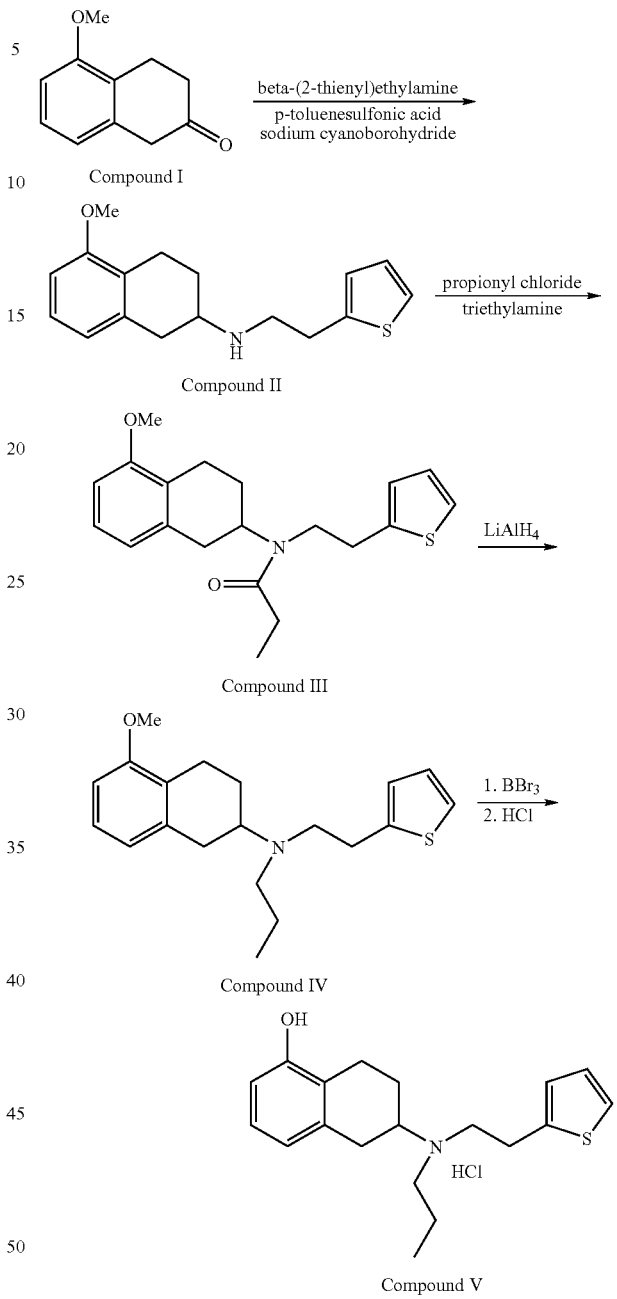

Scheme 1

Another process for preparing racemic rotigotine hydrochloride, which is disclosed in U.S. Pat. No. 4,564,628, is shown in Scheme 2 below. 5-methoxy-2-tetralon (Compound I) is reacted with 3-propylamine in acetic acid and $H_2/PtO_2$ to obtain 1,2,3,4-tetrahydro-5-methoxy-N-propyl-2-naphthaleneamine (Compound VI). This intermediate then is reacted either with 2-thienylacetic acid in presence of borane trimethylamine complex in xylene or with 2-thienylacetyl chloride and lithium aluminum hydride to obtain 1,2,3,4-tetrahydro-5-methoxy-N-propyl-N-[2-(2-thienyl)ethyl]-2-naphthaleneamine (Compound IV). Finally, this intermediate is reacted with boron tribromide, then with HCl, to form the racemic rotigotine hydrochloride (Compound V).

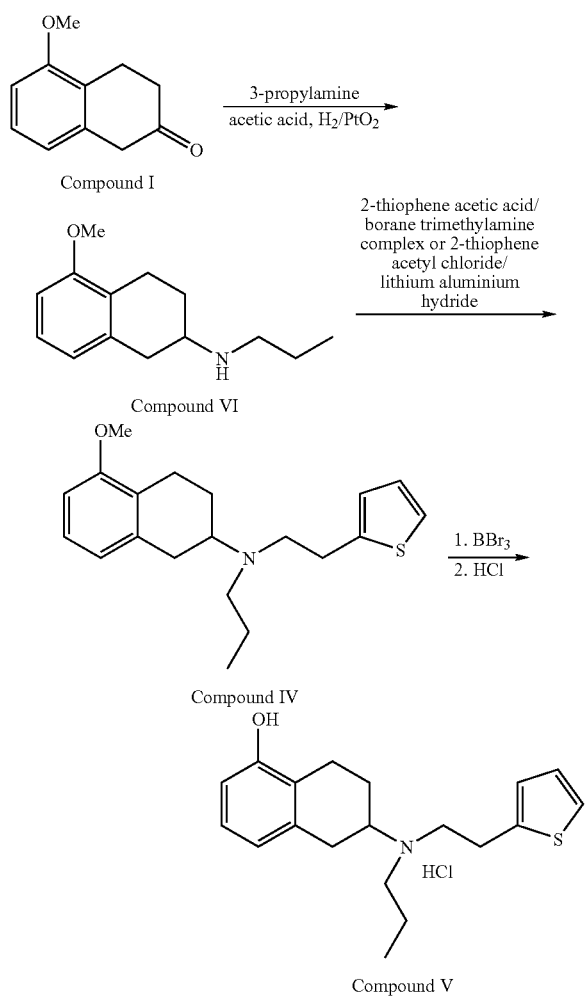

Scheme 2

U.S. Pat. No. 4,885,308 discloses a process for obtaining the two optical isomers of rotigotine by resolving the racemic 2-(N-n-propylamino)-5-methoxytetralin to its two enantiomers, then converting each enantiomer to (+) and (−)-rotigotine, using the process disclosed in U.S. Pat. No. 4,564,628.

The last step in the synthesis of rotigotine, as recited in several patents, such as U.S. Pat. Nos. 4,564,628 and 6,372,920, involves the direct formation of the hydrochloride salt of rotigotine. For instance, none of the five examples of U.S. Pat. No. 6,372,920 detail how the formation of the rotigotine hydrochloride salt is carried out, it is only mentioned that "rotigotine base is converted to its hydrochloride salt form in the usual manner." Example II of U.S. Pat. No. 4,546,628 discloses that the free base of rotigotine is obtained by evaporating a solution of rotigotine to dryness, but the resulting residue was immediately converted to the hydrochloride salt (without isolation). This HCl salt was characterized and reported to have a melting point of 148-150° C.

Although U.S. Pat. Nos. 4,564,628 and 4,885,308 disclose the formation of the free base of rotigotine, using these disclosed procedures results in an oil, not in a more desirable solid form, implying that it is difficult to obtain a crystalline rotigotine base.

According to US Patent Application No. 2004/0048779, rotigotine hydrochloride is converted into rotigotine free base by treating rotigotine hydrochloride with sodium metasilicate or sodium trisilicate for 48 hours, or by treating rotigotine hydrochloride with sodium hydroxide (NaOH) followed by addition of sodium phosphate buffer solution, as disclosed in Examples 3 and 4, respectively. Thus, the preparation of rotigotine base is in situ, the product is not isolated, and its physical properties have not been reported to in these patents or patent publications. On the basis of the above mentioned data, it may be concluded that the previously reported means of synthesizing rotigotine are insufficient for isolating, purifying, and preparing a stable form of the rotigotine base suitable for handling and storing.

Because a transdermal delivery patch contains rotigotine base as opposed to rotigotine hydrochloride, a need exists for a solid rotigotine base, preferably in a crystalline form, that can be used as the active material in transdermal delivery patches.

SUMMARY OF THE INVENTION

The present invention is directed to methods of preparing rotigotine, i.e., 5-hydroxy-2-(N-n-propyl-N-2-thienylethyl)-aminotetralin, as its free base, typically in a solid, crystalline form. This crystalline rotigotine base can be stored at room temperature, purified, and used without the need to convert the base to the hydrochloride salt.

Thus, one aspect of the invention is to provide crystalline rotigotine base having a purity of at least about 98.5%, by weight, based upon the total weight of the sample. In some embodiments, the purity of the rotigotine base is at least about 99.5%, by weight.

In some embodiments, the crystalline form of rotigotine base is Form I, which has a characteristic X-ray powder diffraction pattern comprising peaks at 14.6, 15.2, 15.6, 16.6, 17.0, 19.7, 20.2, 22.6 and 27.8±0.2 degrees 2θ. In various embodiments, the crystalline rotigotine base has an X-ray powder diffraction pattern as depicted in FIG. 1. In some embodiments, the crystalline rotigotine base has an infrared spectrum having absorption bands at 1583, 1466, 1377, 1281, 1203, 1080, 1011, 881, 775 and 700±4 $cm^{-1}$. In specific embodiments, the crystalline rotigotine base has an infrared spectrum as depicted in FIG. 2. In some embodiments, the crystalline rotigotine base has a differential scanning calorimetry (DSC) curve exhibiting peak onset at about 75° C. In specific embodiments, the crystalline rotigotine base has DSC curve as depicted in FIG. 3. In some embodiments, the crystalline rotigotine base has melting point of 75-77° C.

Another aspect of the invention is to provide a method of preparing crystalline rotigotine base comprising:
 (a) dissolving or partially dissolving rotigotine hydrochloride in a first organic solvent and water;
 (b) adding a base to form rotigotine base;
 (c) removing the water and the first organic solvent to form a residue;
 (d) adding water and a second organic solvent to the residue;
 (e) removing the water and the second organic solvent from the mixture of step (d) to obtain crude rotigotine base; and
 (f) crystallizing the crude rotigotine base from a third organic solvent to form crystalline rotigotine base.

In some embodiments, the first organic solvent comprises dichloromethane or ethyl acetate. In various embodiments, the second organic solvent comprises diethyl ether or t-butyl methyl ether. In some embodiments, the third organic solvent is selected from the group consisting of n-pentane, n-hexane, cyclohexane, n-heptane, petroleum ether, and a mixture thereof.

In various embodiments, the base is selected from the group consisting of sodium carbonate, potassium carbonate, sodium bicarbonate, potassium bicarbonate, and combinations thereof.

In some embodiments, the method further comprises collecting, washing, and drying the crystalline rotigotine base. In specific embodiments, the collecting comprises filtering. In some specific embodiments, the washing comprises washing with a fourth organic solvent selected from the group consisting of n-pentane, n-hexane, cyclohexane, n-heptane, petroleum ether, and mixtures thereof.

Another aspect of the invention provides a method of purifying impure rotigotine base comprising:
(a) admixing the impure rotigotine base with an organic solvent;
(b) precipitating purified crystalline rotigotine base from the mixture of (a); and
(c) isolating, washing, optionally milling and drying the purified crystalline rotigotine base.

In some embodiments the organic solvent of step (a) is selected from the group consisting of n-pentane, n-hexane, cyclohexane, n-heptane, petroleum ether, and mixtures thereof. In a specific embodiment, the organic solvent is n-hexane.

Yet another aspect of the invention provides a method for the manufacture of transdermal patches using rotigotine base Form I.

DETAILED DESCRIPTION OF THE INVENTION

Disclosed herein is crystalline rotigotine base, which is alternatively and interchangeably called throughout this disclosure solid rotigotine base or polymorph Form I of rotigotine base, and methods of preparing crystalline rotigotine base and purifying crystalline rotigotine base. The disclosed rotigotine base can be stored room temperature without need to convert it to a salt form.

Figure 1:
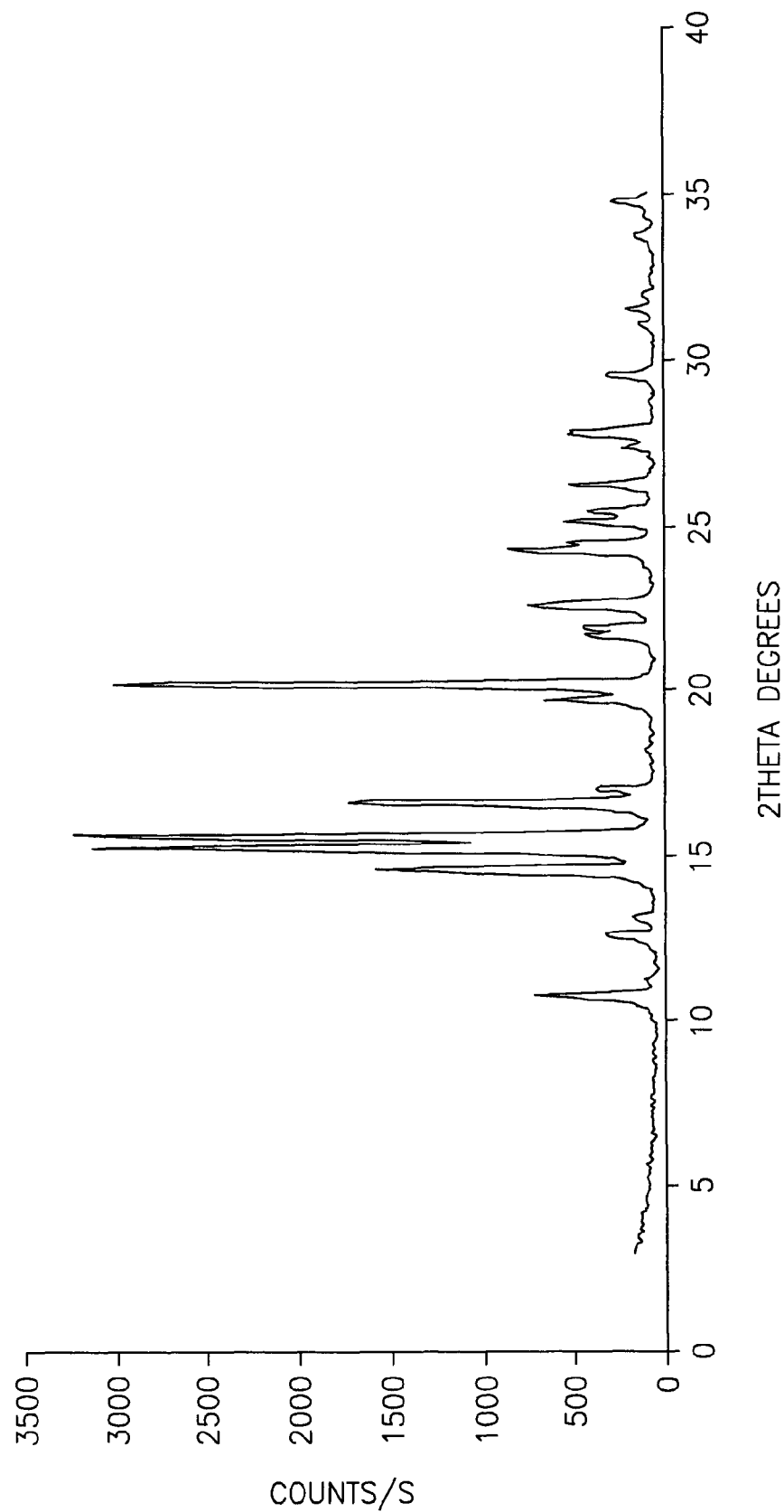
FIG. 1 shows the X-ray powder diffraction pattern of rotigotine base crystalline Form I.

The precipitation of crystalline rotigotine base can be cumbersome, and is not a simple matter, because an oil can be obtained without using proper crystallizing conditions, such as solvent and concentration conditions (see examples 3, 4 and 5). Rotigotine base crystalline Form I produces a unique X-ray powder diffraction pattern, as depicted in FIG. 1. The strong diffraction peaks at 14.6, 15.2, 15.6, 16.6, 17.0, 19.7, 20.2, 22.6 and 27.8±0.2 degrees 2θ are most characteristic of this form. The X-ray powder diffraction peak positions and intensities exhibited by rotigotine base crystalline Form I are listed in Table 1.

TABLE 1

| Peak position 2θ degrees | Relative intensity $I/I_0$ |
|---|---|
| 10.7 | 7.4 |
| 11.2 | 1.1 |
| 12.6 | 8.6 |
| 13.1 | 6.2 |
| 14.6 | 52.8 |
| 15.2 | 43.5 |
| 15.6 | 49.5 |
| 16.6 | 36.0 |
| 17.0 | 13.1 |
| 18.2 | 1.9 |
| 19.7 | 27.6 |
| 20.2 | 100.0 |
| 21.7 | 5.0 |
| 21.9 | 5.2 |
| 22.6 | 25.9 |
| 24.3 | 10.9 |
| 24.5 | 6.8 |
| 25.1 | 15.4 |
| 25.4 | 9.3 |
| 26.2 | 10.4 |
| 27.3 | 5.6 |
| 27.8 | 21.4 |
| 28.6 | 1.6 |
| 29.5 | 9.9 |
| 31.0 | 1.4 |
| 31.5 | 6.5 |
| 31.9 | 4.1 |
| 33.7 | 5.6 |
| 34.7 | 2.4 |

Figure 2:
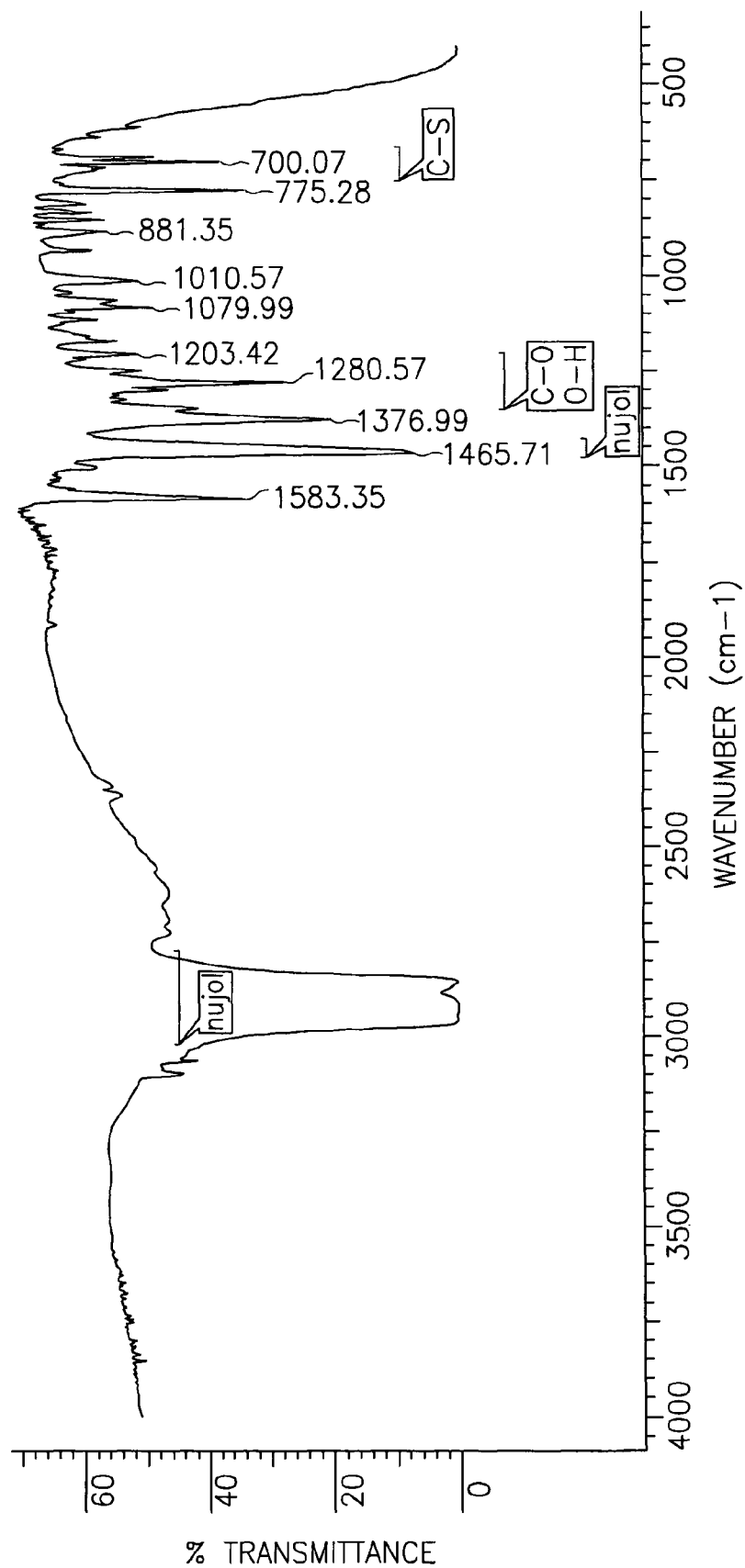
FIG. 2 shows the infrared spectrum of rotigotine base crystalline Form I.

Crystalline rotigotine base Form I further produces a unique infrared spectrum as depicted in FIG. 2. The characteristic infrared spectrum absorption bands of the crystalline rotigotine base Form I are at 1583, 1466, 1377, 1281, 1203, 1080, 1011, 881, 775 and 700±4 cm$^{-1}$.

Figure 3:
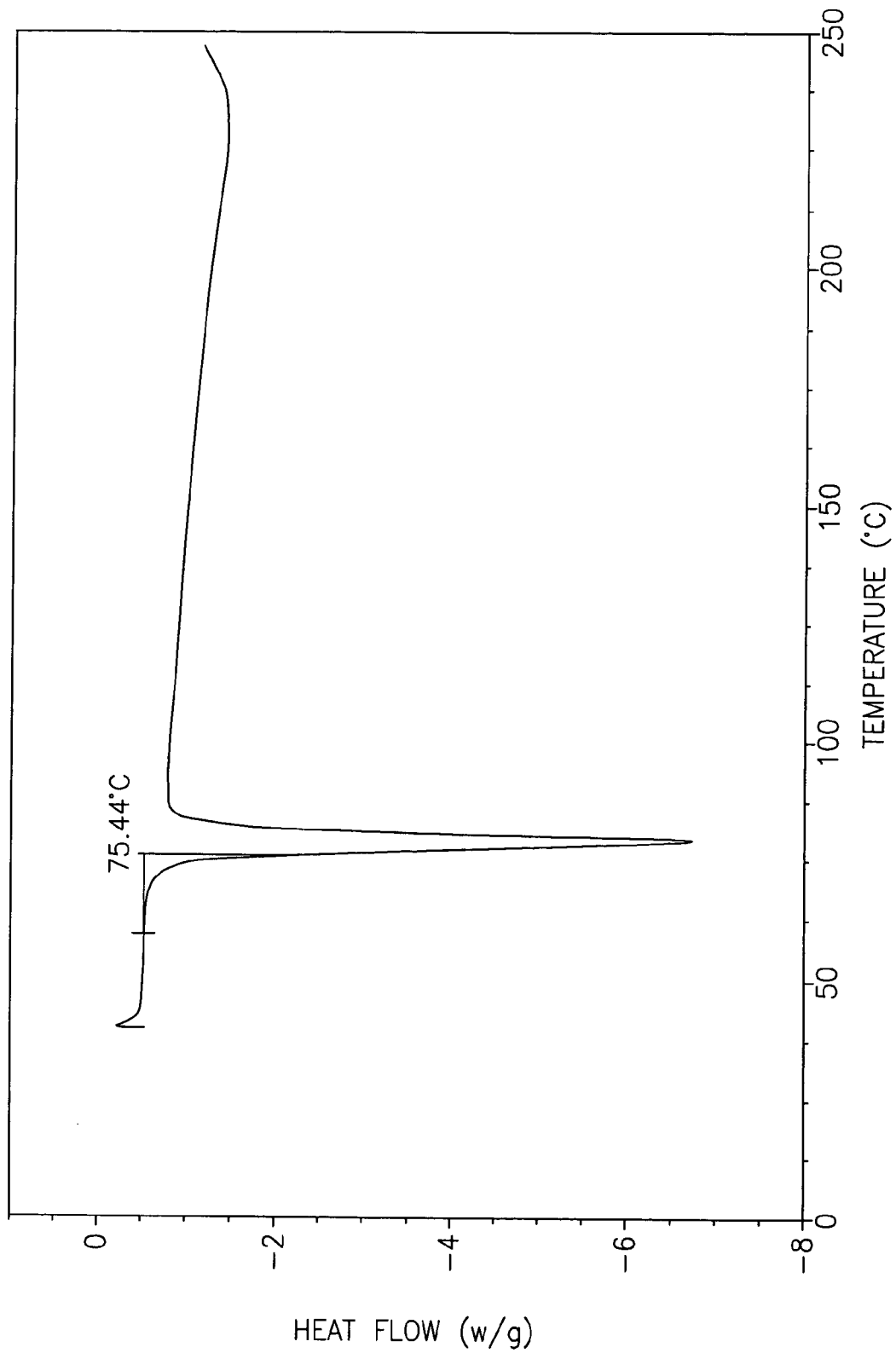
FIG. 3 shows the differential scanning calorimetry (DSC) curve of rotigotine base crystalline Form I.

Further, rotigotine base crystalline Form I produces a characteristic DSC curve, exhibiting peak onset at about 75±1° C., as depicted in FIG. 3. The melting point of the rotigotine base Form I of the present invention is 75-77° C.

Figure 4:
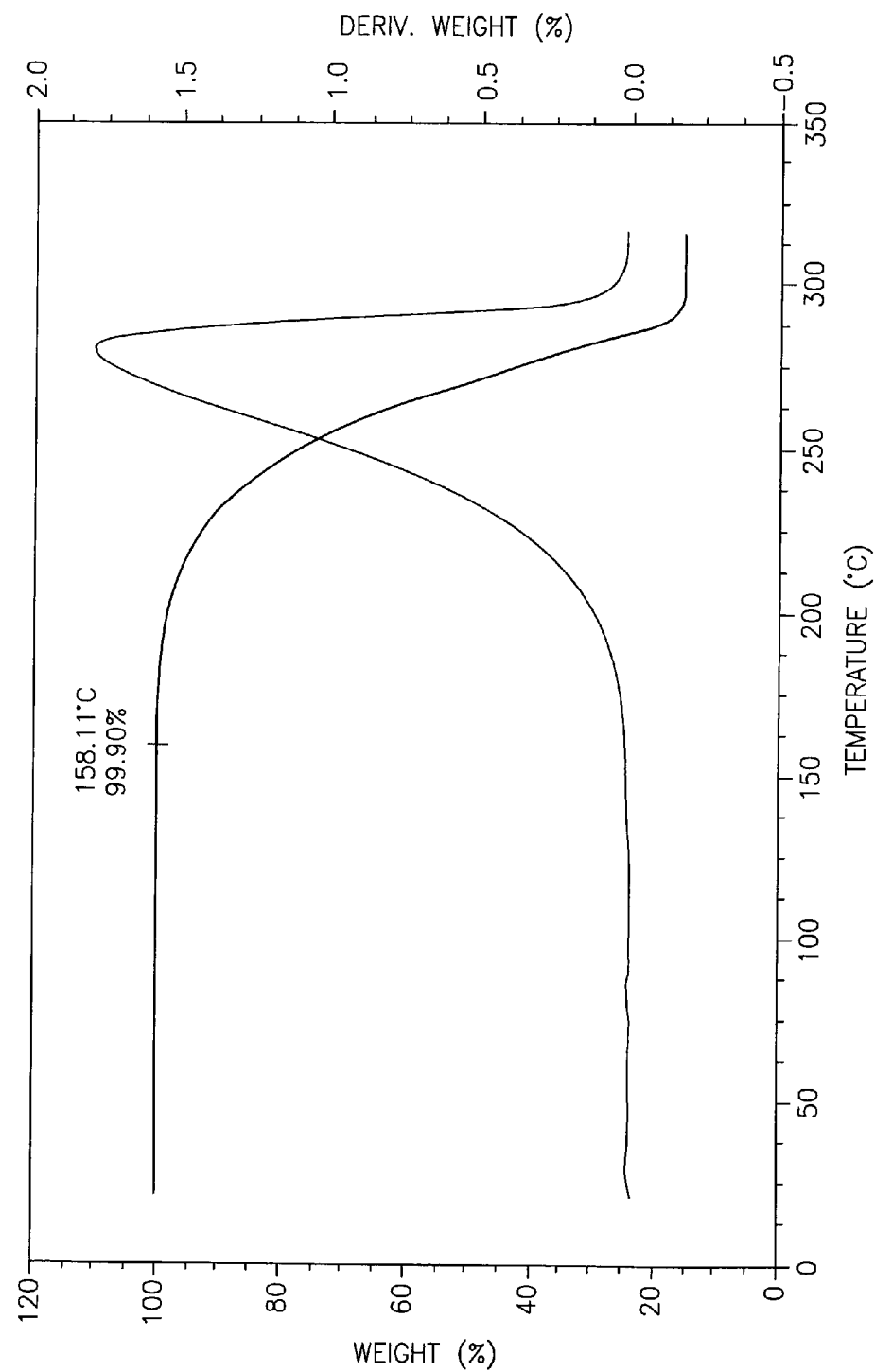
FIG. 4 shows the thermogravimetric analysis (TGA) curve of rotigotine base crystalline Form I.

Rotigotine base crystalline form I produces a TGA curve as depicted in FIG. 4. It may be understood from analyzing the TGA curve of the crystalline rotigotine base Form I, that the compound (a) does not decompose on heating, (b) does not lose any volatile molecule (e.g., a solvent molecule), namely the crystalline rotigotine base form I is not a solvate or a hydrate, and (c) is thermally stable.

The present invention discloses a method of preparing crystalline rotigotine base comprising:
(a) dissolving or partially dissolving rotigotine hydrochloride in a first organic solvent and water;
(b) adding a base to form rotigotine base;
(c) removing the water and the first organic solvent to form a residue;
(d) adding water and a second organic solvent to the residue;
(e) removing the water and the second organic solvent from the mixture of step (d) to obtain rotigotine base; and
(f) crystallizing the rotigotine base obtained in step (e) from a third organic solvent to form crystalline rotigotine base. In some embodiments, the method further comprises collecting, washing, and drying the crystalline rotigotine base.

The term "dissolving" or "partially dissolving" as used herein refers to preparing a solution of the rotigotine base or hydrochloride salt in an organic solvent. In cases where the rotigotine does not fully dissolve in the organic solvent, the resulting mixture is a partial solution.

The first organic solvent is typically dichloromethane, but can be also ethyl acetate. The second organic solvent is typically diethyl ether, but can be also t-butyl methyl ether. The third organic solvent is typically n-pentane, n-hexane, cyclohexane, n-heptane, petroleum ether, or a mixture thereof.

The concentration of the solution or partial solution of impure rotigotine base is typically up to about 0.5 mg/mL. The concentration can be about 0.09 mg/mL to about 0.1 mg/mL. In some cases, the concentration can be about 0.01 mg/mL to about 0.4 mg/mL, about 0.05 mg/mL to about 0.3 mg/mL, about 0.07 mg/mL to about 0.2 mg/mL, or about 0.08 mg/mL to about 0.15 mg/mL.

The solution or partial solution optionally can be cooled prior to or during crystallization. Typically the solution or partial solution is crystallized at ambient (about 22 to about 25° C.) temperatures. Other temperatures include about 10° C. to about 25° C. and about 15° C. to about 25° C.

The base that is added to the solution or partial solution can be any inorganic or organic base compatible with rotigotine. By "compatible" is meant that the base does not chemically alter the structure of rotigotine via isomerization, epimerization, dehydration, or the like. Specific bases that can be used include, but are not limited to, sodium bicarbonate, sodium carbonate, potassium carbonate, potassium bicarbonate, and combinations thereof. Preferably, the base is sodium bicarbonate or sodium carbonate.

Rotigotine base or rotigotine free base refers to a form of rotigotine which does not have an associate acid addition salt, e.g., hydrochloride, hydrobromide, citrate, sulfate, phosphate, or the like.

The removal of water and the first organic solvent to form the residue can be via a number of means, including separating the aqueous and organic phases, then evaporating the organic phase to form the residue. Alternatively, the water and organic solvent can simultaneously be removed via evaporation, optionally under reduced pressure. In a preferred embodiment, the water and organic phases are separated and the organic solvent of the organic phase is removed or partially removed via evaporation.

The crystals of rotigotine base can be collected using a number of techniques, but preferably are collected via filtration. The crystals then can be washed with a suitable organic solvent, such as n-pentane, n-hexane, cyclohexane, n-heptane or petroleum ether.

Another aspect of the invention provides a method of purifying impure rotigotine base comprising:
(a) admixing the impure rotigotine base with an organic solvent;
(b) precipitating purified crystalline rotigotine base from the mixture of (a); and
(c) isolating, washing, optionally milling and drying the crystalline rotigotine base.

The term "impure," as used herein, refers to a compound, typically rotigotine base, having up to 93% by weight of that compound in the sample.

The term "pure," as used herein, refers to a compound, typically rotigotine base, having greater than 94% by weight of that compound in the sample. In some embodiments, rotigotine base has a purity of at least 98.5%, at least 99.5%, or at least 99.8% by weight. The purity of a sample can be determined using techniques known in the art, including liquid and gas chromatography.

Typically, the organic solvent used for precipitating the impure rotigotine base is selected from the group consisting of n-pentane, n-hexane, cyclohexane, n-heptane, petroleum ether, and mixtures thereof. A preferred organic solvent is n-hexane.

Another aspect of the invention provides a method of manufacturing a transdermal patch of rotigotine base comprising using crystalline rotigotine base as disclosed herein to prepare a transdermal patch. In general, means of making rotigotine transdermal patches are disclosed in U.S. Pat. No. 6,929,801, which is incorporated by reference in its entirety herein. In some cases, the crystalline rotigotine base is polymorph Form I.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illustrate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

EXAMPLES

Although, the following examples illustrate the practice of the present invention in some of its embodiments, the examples should not be construed as limiting the scope of the invention. Other embodiments will be apparent to one skilled in the art from consideration of the specification and examples. It is intended that the specification, including the examples, is considered exemplary only without limiting the scope and spirit of the invention.

General Description of the Equipment

X-ray diffraction data were acquired using a PHILIPS X-ray diffractometer model PW1050-70. System description: $K\alpha1=1.54178$ Å, voltage 40 kV, current 28 mA, diversion slit=1°, receiving slit=0.2 mm, scattering slit=1° with a Graphite monochromator. Measurements of $2\theta$ values typically are accurate to within ±0.2 degrees. Experiment parameters: pattern measured between 2θ=3° and 2θ=30° with 0.05° increments; count time was 0.5 second per increment.

Infrared spectra were run on Nicolet Fourier-transform infrared spectrometer model Avatar 360, with Omnic software version 5.2. All samples were run as KBr disks. The current infrared measurements are accurate to within 4 cm$^{-1}$.

Differential scanning calorimetry (DSC) measurements were run on TA instruments model Q1000, with Universal software version 3.88. Samples were analyzed inside crimped 40 μl Aluminum pans. The heating rate was 10° C./min.

Thermogravimetric analysis (TGA) is the measure of the thermally induced weight loss of a material as a function of the applied temperature. The TGA measurement was performed using a TA instruments Q500 Thermal analyzer with Universal Software (version 3.88). Samples were analyzed inside platinum baskets at heating rate of 5° C./minute.

Reference Example 1

This example demonstrates the preparation of rotigotine base from rotigotine hydrochloride in a similar fashion to example 4 of US Patent Application No. 2004/0048779.

A mixture of 1.76 g rotigotine hydrochloride (5 mmol) in 20 ml water and 20 ml ethyl acetate, having a pH of about 3, was stirred at room temperature and titrated with NaOH 0.1N until complete dissolution occurred at about pH of 6.5. The phases were separated and the organic phase was dried with magnesium sulfate and the solvent was evaporated under reduced pressure to dryness obtain 1.52 g (4.8 mmol) of a viscous oil of rotigotine base in 96% yield.

Example 2

This example demonstrates the preparation of rotigotine base Form I.

A reaction vessel, equipped with a magnetic stirrer, a dropping funnel, and a pH meter was charged with 50 g of rotigotine hydrochloride at ambient temperature, and 750 mL of dichloromethane and 250 mL of water were added. The resulting mixture was stirred for about 20 minutes and the pH was adjusted to 6.5 by dropwise addition of about 170 mL of a 5% solution of sodium bicarbonate. The phases were separated, and the organic phase was washed twice with 250 mL each of water. The aqueous phase was washed with dichloromethane and the organic phases were combined and evaporated under vacuum to obtain a solid. Water (250 mL) was added to the solid and the volume was concentrated by distillation. Diethyl ether (10 mL) was added to the residue and evaporated to obtain a solid. n-hexane (500 mL) was added to the solid and the mixture was stirred overnight at room temperature. Crystals were formed and subsequently filtered, washed with 50 mL of n-hexane, and dried under vacuum to afford 42 g of crystalline rotigotine base Form I in 94% yield, having a purity of 99.9%, by HPLC.

Example 3

This example describes an attempt to prepare crystalline rotigotine base from rotigotine hydrochloride.

A reaction vessel, equipped with a magnetic stirrer, a dropping funnel, and a pH meter, was charged with 2 g of rotigotine hydrochloride at ambient temperature and 20 mL of dichloromethane and 30 mL of water were added. The mixture was stirred for about 20 minutes and the pH was adjusted to 7.8 by dropwise addition of about 15 mL of a 5% solution of sodium bicarbonate. The phases were separated and the organic phase was washed with 15 mL of water. The aqueous phase was washed with 20 mL of dichloromethane and the organic phases were combined. About 2 mL of diethyl ether was added to the organic phase and the mixture was cooled to 4° C. and stirred overnight at that temperature. An oil was formed, which was isolated and dissolved in acetone. Water was added and the mixture was lyophilized but failed to yield a crystalline material.

Examples 4-5

These examples demonstrate other attempts to prepare crystalline rotigotine base from rotigotine hydrochloride.

The same procedure, as described in Example 2, was repeated to obtain a solution of rotigotine base in dichloromethane. Then, about 2 mL of n-hexane (Example 4) or petroleum ether (Example 5) was added to the organic phase, and the mixture was cooled to 4° C. and stirred overnight at that temperature. An oil was formed, which was isolated and dissolved in ethanol. Water was added and the mixture was lyophilized but failed to yield a crystalline material.

Example 6

This example demonstrates the preparation of solid rotigotine base from rotigotine hydrochloride.

A reaction vessel, equipped with a magnetic stirrer, a dropping funnel, and a pH meter, was charged with 5 g of rotigotine hydrochloride (14 mmol) at ambient temperature, and 75 mL of dichloromethane was added. The mixture was stirred for about 20 minutes and the pH was adjusted to 8 by dropwise addition of about 27 mL of a 5% solution of sodium carbonate. The mixture was stirred for 4 hours after which time the phases were separated and the aqueous phase was washed with 25 mL of dichloromethane. The organic phases were combined, washed with 2×25 mL water and dried over magnesium sulfate. The solvent was evaporated and diethyl ether (5 mL) was added to the thus formed residue and evaporated using rotary evaporator. Then, n-hexane was added to the thus formed residue and mixed until a white solid was formed. The solid was obtained by filtration, milled, washed with n-hexane (10 ml) and dried in vacuum to obtain 4.2 g (95% yield) of solid rotigotine base.

What is claimed is:

1. A method of preparing the crystalline rotigotine base having an X-ray powder diffraction pattern comprising peaks at 14.6, 15.2, 15.6, 16.6, 17.0, 19.7, 20.2, 22.6 and 27.8 degrees 2θ, the method comprising:
    (a) dissolving or partially dissolving rotigotine hydrochloride in a first organic solvent and water;
    (b) adding a base to the mixture of (a) to form rotigotine base;
    (c) removing the water and the first organic solvent of (b) to form a residue;
    (d) adding water and a second organic solvent to the residue;
    (e) removing the water and the second organic solvent from the mixture of step (d) to obtain crude rotigotine base; and
    (f) crystallizing the crude rotigotine base from a third organic solvent selected from n-pentane, n-hexane, cyclohexane, n-heptane, petroleum ether, and mixtures thereof, to form crystalline rotigotine base.

2. The method of claim 1 further comprising (g) one or more of collecting, washing, and drying the crystalline rotigotine base.

3. The method of claim 2, wherein the washing comprises washing with a fourth solvent selected from n-pentane, n-hexane, cyclohexane, n-heptane, petroleum ether, and mixtures thereof.

4. The method of claim 2, wherein the fourth solvent comprises n-hexane.

5. The method of claim 1, wherein the first organic solvent comprises dichloromethane.

6. The method of claim 1, wherein the second organic solvent comprises diethyl ether.

7. The method of claim 1, wherein the third organic solvent is n hexane.

8. The method of claim 1, wherein the rotigotine base in the solution or partial solution has a concentration of up to about 0.5 mg/mL.

9. The method of claim 1, wherein the base is selected from sodium carbonate, potassium carbonate, sodium bicarbonate, potassium bicarbonate, and combinations thereof.

10. A method of purifying impure rotigotine base comprising:
    (a) admixing the impure rotigotine base with an organic solvent selected from n-pentane, n-hexane, cyclohexane, n-heptane, petroleum ether, and mixtures thereof;
    (b) precipitating purified crystalline rotigotine base from the mixture of (a); and
    (c) isolating, washing, drying, and optionally milling the crystalline rotigotine base.

11. The method of claim 10, wherein the organic solvent of step (a) comprises n-hexane.

* * * * *